(12) United States Patent
Polizzotto et al.

(10) Patent No.: US 6,184,040 B1
(45) Date of Patent: Feb. 6, 2001

(54) DIAGNOSTIC ASSAY SYSTEM AND METHOD

(75) Inventors: Leonard Polizzotto, Stow; Thomas Demerle, II, Boston; James A. Murphy, III, Malden, all of MA (US); Peter H. Roth, Quechee, VT (US); Philip R. Norris, North Reading; Robert J. Wadja, Wellesley, both of MA (US)

(73) Assignee: Polaroid Corporation, Cambridge, MA (US)

( * ) Notice: Under 35 U.S.C. 154(b), the term of this patent shall be extended for 0 days.

(21) Appl. No.: 09/238,212

(22) Filed: Jan. 27, 1999

Related U.S. Application Data (60) Provisional application No. 60/074,527, filed on Feb. 12, 1998, and provisional application No. 60/104,150, filed on Oct. 14, 1998.

(51) Int. Cl.⁷ .......................... G01N 35/00; G01N 21/00; G01N 21/03; G01N 21/29; G01N 15/06

(52) U.S. Cl. .................. 436/43; 436/164; 436/165; 422/82.05; 422/68.1; 422/63; 422/50; 422/55; 422/91; 422/119

(58) Field of Search .................. 422/68.1, 63, 82.05, 422/58, 82.08, 52; 436/43, 164, 165, 172; 250/458.1, 361 C (56) References Cited

U.S. PATENT DOCUMENTS

| | | | |
|---|---|---|---|
| 3,390,962 | 7/1968 | Goldsmith | 23/253 |
| 3,415,361 | 12/1968 | Adams, Jr. et al. | 206/47 |
| 3,680,967 | 8/1972 | Engelhardt | 356/246 |
| 3,788,205 | 1/1974 | Pasieka et al. | 95/93 |
| 3,865,548 | 2/1975 | Padawer | 23/230 |
| 4,111,754 | 9/1978 | Park | 195/127 |
| 4,233,029 | 11/1980 | Columbus | 23/230 |
| 4,254,083 | 3/1981 | Columbus | 422/55 |
| 4,264,560 | 4/1981 | Natelson | 422/58 |
| 4,271,119 | 6/1981 | Columbus | 422/50 |
| 4,302,313 | 11/1981 | Columbus | 204/195 R |
| 4,310,399 | 1/1982 | Columbus | 204/195 R |
| 4,323,536 | 4/1982 | Columbus | 422/56 |
| 4,371,498 | 2/1983 | Scordato et al. | 422/102 |
| 4,396,579 | 8/1983 | Schroeder et al. | 422/52 |
| 4,413,407 | 11/1983 | Columbus | 29/825 |
| 4,426,451 | 1/1984 | Columbus | 436/518 |
| 4,439,526 | 3/1984 | Columbus | 436/180 |
| 4,510,393 | 4/1985 | Sell et al. | 250/475 |
| 4,549,952 | 10/1985 | Columbus | 204/416 |
| 4,587,221 | 5/1986 | Cais et al. | 436/500 |
| 4,608,231 | 8/1986 | Witty et al. | 422/61 |
| 4,675,299 | 6/1987 | Witty et al. | 436/165 |
| 4,757,004 | 7/1988 | Houts et al. | 435/7 |
| 4,767,719 | * 8/1988 | Finlan | 436/501 |
| 4,772,453 | 9/1988 | Lisenbee | 422/52 |
| 4,797,259 | 1/1989 | Matkovich et al. | 422/101 |
| 4,833,087 | 5/1989 | Hinckley | 435/287 |
| 4,863,689 | 9/1989 | Leong et al. | 422/52 |
| 4,906,439 | 3/1990 | Grenner | 422/56 |
| 4,918,025 | 4/1990 | Grenner | 436/165 |
| 4,948,564 | 8/1990 | Root et al. | 422/101 |
| 4,948,975 | 8/1990 | Erwin et al. | 250/361 |
| 4,959,324 | 9/1990 | Ramel et al. | 436/169 |
| 4,973,549 | 11/1990 | Khanna et al. | 435/11 |
| 4,978,502 | 12/1990 | Dole et al. | 422/58 |

(List continued on next page.)

FOREIGN PATENT DOCUMENTS

WO 97/27463   3/1997   (WO).

*Primary Examiner*—Jill Warden
*Assistant Examiner*—Brian R. Gordon
(74) *Attorney, Agent, or Firm*—Leslie Payne (57) ABSTRACT

A diagnostic assay device comprising a housing assembly and an image recording material housed therein that is exposed by a luminescent read-out signal generated by a luminescent activity triggered in response to displacement of a liquid carrier assembly carrying an analyte of interest with a reservoir containing an assay solution.

16 Claims, 7 Drawing Sheets

U.S. PATENT DOCUMENTS

| | | | |
|---|---|---|---|
| 4,985,631 | 1/1991 | Wannlund et al. | 250/361 |
| 4,987,085 | 1/1991 | Allen et al. | 324/407 |
| 5,011,663 | 4/1991 | Innocenti | 422/102 |
| 5,035,866 | 7/1991 | Wannlund | 422/102 |
| 5,053,197 * | 10/1991 | Bowen | 422/58 |
| 5,063,090 | 11/1991 | Wannlund | 427/384 |
| 5,073,484 | 12/1991 | Swanson et al. | 435/7.92 |
| 5,075,077 | 12/1991 | Durley, III et al. | 422/56 |
| 5,093,268 | 3/1992 | Leventis et al. | 436/172 |
| 5,098,661 | 3/1992 | Froehlich et al. | 422/102 |
| 5,100,621 | 3/1992 | Berke et al. | 422/61 |
| 5,132,086 | 7/1992 | Allen et al. | 422/56 |
| 5,159,197 | 10/1992 | Wannlund | 250/328 |
| 5,164,301 | 11/1992 | Thompson et al. | 435/29 |
| 5,167,922 | 12/1992 | Long | 422/58 |
| 5,188,965 | 2/1993 | Wannlund | 436/165 |
| 5,219,762 | 6/1993 | Katamine et al. | 436/518 |
| 5,244,630 | 9/1993 | Khalil et al. | 422/52 |
| 5,281,395 * | 1/1994 | Markart et al. | 422/82.05 |
| 5,319,436 | 6/1994 | Manns et al. | 356/246 |
| 5,332,549 | 7/1994 | MacIndoe, Jr. | 422/63 |
| 5,355,215 | 10/1994 | Schroeder et al. | 356/317 |
| 5,399,316 * | 3/1995 | Yamada | 422/58 |
| 5,411,893 | 5/1995 | Eden et al. | 436/165 |
| 5,418,171 | 5/1995 | Kimura et al. | 436/518 |
| 5,441,894 | 8/1995 | Coleman et al. | 436/518 |
| 5,457,527 | 10/1995 | Manns et al. | 356/246 |
| 5,460,778 | 10/1995 | Macindoe, Jr. | 422/63 |
| 5,482,839 | 1/1996 | Ashihara et al. | 435/7.9 |
| 5,510,244 * | 4/1996 | Inoue et al. | 435/26 |
| 5,552,276 | 9/1996 | Mochida | 435/6 |
| 5,657,118 | 8/1997 | Lee | 356/246 |
| 6,027,943 * | 2/2000 | Kang et al. | 436/518 |
| 6,066,243 * | 5/2000 | Anderdon et al. | 204/403 |
| 6,096,268 * | 8/2000 | Inbar | 422/56 |

* cited by examiner

DIAGNOSTIC ASSAY SYSTEM AND METHOD

CROSS-REFERENCE TO RELATED PATENT APPLICATIONS

The present application is related to: copending U.S. provisional patent application, entitled "Diagnostic Assay System and Method" filed Feb. 12, 1998, and having Ser. No. 60/074,527; copending U.S. non-provisional patent application, (Atty. Dkt. No. 8336), entitled "Diagnostic Assay Device" filed concurrently herewith; and, copending provisional patent application entitled "Method and Apparatus For Performing Diagnostic Testing" filed Oct. 14, 1998, and having Ser. No. 60/104,150.

BACKGROUND

The present invention relates generally to diagnostic assay systems and methods and, in particular, to hand-held diagnostic assay systems and methods for conducting signal generating activities and recording the same on image recording material.

Detecting the presence or absence of generated signals, such as of the luminescent and fluorescent type as a means of indicating the presence or absence of certain biological and/or chemical activities is well-known. Examples of these approaches include use of single-sample luminometers fitted with photographic multipliers; single-sample luminometers fitted solid-state detectors; multiple sample luminometers; automatic luminometers with imaging systems based on CCD cameras; and photographic camera type luminometers for recording luminescent activity on conventional and self-developing film. Heretofore, many of the above noted approaches are rather expensive and difficult to use due to their complicated construction including utilization of electronics as well as the requirements of an associated source of power. Further examples of known approaches in this field include those described generally in U.S. Pat. Nos. 4,863,689, and 5,035,866.

Despite the existence of a wide variety of known diagnostic testing systems and approaches, however, it is, nevertheless, desired to improve upon the overall ease, versatility, and reliability of such systems and their testing procedures, as well as reduce overall costs associated with their construction and use.

SUMMARY OF THE INVENTION

In accordance with the present invention, provision is made for a diagnostic assay system operable for conducting assay operations and recording signals generated therefrom on a film assemblage. Included in the system is a processor comprising a hand-held housing assembly having at least one fluid access port and a film assemblage having its image recording area retained within a light-tight compartment therein. The film assemblage is removable therefrom through an exit in the housing. Preferably, the film is of the self-developing type and its image recording area is positionable at an exposure station within the housing assembly. A sample carrier assembly is movable within the housing assembly between a fluid accessing position and an exposing position. The carrier assembly carries at a least fluid reservoir assembly for use in conjunction with a diagnostic test element. When the sample carrier is in its fluid accessing position, a sample test fluid perhaps containing an analyte of interest can be introduced through the access port and into the reservoir assembly wherein it is selectively retained. Triggering devices in the housing upon movement of the sample carrier triggers flow of the fluid from the reservoir to the test strip, thereby commencing a signal generating activity if the analyte of interest is present. This movement results in the test strip being at the exposing position over an aperture in registry with the image recording area, whereby the generated signal exposes the film.

In an illustrated embodiment, provision is made for a fluid reservoir assembly having at least one opening for forming a meniscus for holding the fluid and then allowing release of the fluid in response to a triggering action effected upon movement of the sample carrier assembly to the exposing position.

In an illustrated embodiment, provision is made for a sample carrier assembly that holds the fluid reservoir assembly and is in operative relationship to an associated assay element, whereby a triggering assembly in the housing assembly effects release of the fluid retained in the reservoir to the assay element while the carrier assembly moves from first to second positions, thereby commencing a signal generating event if the fluid contains an analyte of interest.

In another illustrated embodiment, the sample carrier uncovers an exposure aperture in the housing assembly while the carrier assembly is advanced to the second position.

In an illustrated embodiment, provision is made for use of a film assemblage of the self-developing type wherein at least a single film unit is withdrawn from the housing assembly past film processing means located in the housing assembly so that the hand-held system is otherwise disposable.

In another illustrated embodiment, provision is made for a second fluid reservoir assembly and corresponding triggering means for triggering the release of a control fluid introduced and retained in the second reservoir to an associated assay strip in response to the sample carrier moving to the exposing position; whereby a luminescent reaction of an analyte of interest exposes the film.

The present invention contemplates a method of conducting a diagnostic assay of a test fluid and recording the results thereof by recording signals capable of exposing an image recording material if the test fluid contains an analyte of interest. The image recording material is, preferably, of the self-developing type. Included in such a method are the steps of: providing at least one self-developing film strip; providing a processor including a hand-held housing assembly having at least a fluid access port allowing introduction of the test fluid to a fluid reservoir assembly therefor and an associated diagnostic element in operative relationship thereto; housing the film assemblage within a light-tight compartment of the housing assembly so that an exposure aperture therein allows exposure of the film assemblage; carrying the fluid reservoir and diagnostic element in the housing from a first position to a second position; triggering the reservoir during such carrying step to release the retained fluid to the diagnostic element whereby if the fluid contains an analyte of interest a signal recordable on the film is generated; exposing the film assemblage through the exposure aperture when the diagnostic element is at the second position. In another illustrated embodiment, the method further includes the step of processing the exposed film as the latter is withdrawn from the housing assembly.

In another illustrated embodiment, the step of carrying the fluid reservoir assembly and the diagnostic element is carried out by a sample carrier assembly which in the first position covers the exposure aperture and allows introduction of test fluid to the reservoir; and, in the second position uncovers the exposure aperture.

In another illustrated embodiment of the last noted type, provision is made for triggering release of the fluid from the reservoir in response to movement of the carrier assembly from the first to the second positions.

Another embodiment defines a diagnostic testing method which includes the step of: introducing a test fluid into a reservoir; retaining the test fluid therein by reason of surface tension; triggering the release of the fluid from the reservoir onto a diagnostic element in adjacent relationship thereto by causing the retained fluid to contact a diagnostic element and/or applying force to the reservoir and/or the test fluid which is sufficient to overcome the surface tension, the fluid is released onto the diagnostic element, whereby if released fluid contains an analyte of interest a signal is generated that is capable of exposing the film; and, exposing the film to the generated signal.

In another illustrated embodiment, the latent image of the generated signal is processed by passing the film in operative relationship to a film processing means in the housing as the film is withdrawn from the housing.

It is an object of the present invention to provide an improved method and system for conducting and recording luminescent reactions, wherein the results are instantly and reliably recorded by an operator.

It is another object of the present invention to provide an improved method and system for conducting and recording luminescent reactions in a hand-held assay processor using self-developing type film.

It is another object of the present invention to provide an improved method and system for conducting and recording luminescent reactions in a hand-held assay processor wherein the testing and exposing of the film are achieved in a simple and reliable manner.

It is another object of the present invention to provide improved method and system of the above type, whereby a diagnostic processor is operated without a power source for conducting diagnostic assays in a manner that provides reliable hard copy records of the diagnostic testing performed.

It is another object of the present invention to provide an improved method and system for conducting and recording luminescent reactions which is economically operated and manufactured.

It is another object of the present invention to provide for improved method and system of the above type that minimizes the number of components thereof and simplifies the operation thereof.

The above and other objects and features of the present invention will become apparent when reading the following description taken in conjunction with the accompanying drawings were in like parts or designated by like reference numerals throughout the several views.

DETAILED DESCRIPTION

Reference is made to FIGS. 1–5 for illustrating one preferred embodiment of a disposable, preferably single-use photodiagnostic assay system 10 made according to the present invention. The system 10 includes a processor housing assembly 12 which houses biological diagnostic assay devices and a film assemblage 16; preferably of the self-developing type. Test sample fluid (not shown) is introduced to the processor housing assembly 12 through a pair of test and control ports 18, 19; respectively. Signal generating activity of the chemiluminescent type is generated if a particular analyte being tested for is present, in sufficient amounts, in the test fluid sample that reacts with a diagnostic test element therefor. In this embodiment, the film assemblage 16 includes a single frame of so-called integral type film, but may be peel-apart as well. Essentially, the film assemblage 16 includes a pod 16a at a leading end of an exposable area 16b and a fluid trap 16c at a trailing end of the exposable area for capturing excess fluid. A protruding tab portion 16d is attached as an integral part of the unit and is of flexible plastic sheet, such as MYLAR™. The tab portion 16d has a sufficient length to extend from the housing assembly 12 so as to be pulled in a manner to be discussed. The film assemblage 16, per se, does not form an aspect of the present invention. However, reference is made to copending patent applications 08/958,902; 08/959,361 for better describing the construction of such a film assemblage so that its use in the present invention will be understood. Reference is also made to 08/738,772 for a description of a photographic apparatus in which the film assemblage can be used. Essentially, the film assemblage 16 is retained within the housing assembly and is strong enough to be pulled from a film exit 17 by an operator pulling on the tab 16d. The film assemblage 16 is completely withdrawn to initiate development of a latent image and thereby provide a permanent hard copy record of the test. While the preferred embodiment discloses the above noted film format, clearly the present invention envisions other types of image recording systems. For instance, the film assemblage can be of the self-developing type, such as CAPTIVA™ manufactured by Polaroid Corporation. The withdrawal causes initiation of the processing of latent images on the film generated by chemiluminescent signals. The processor housing assembly can be disposed of following completion of the film withdrawal.

Figure 4:
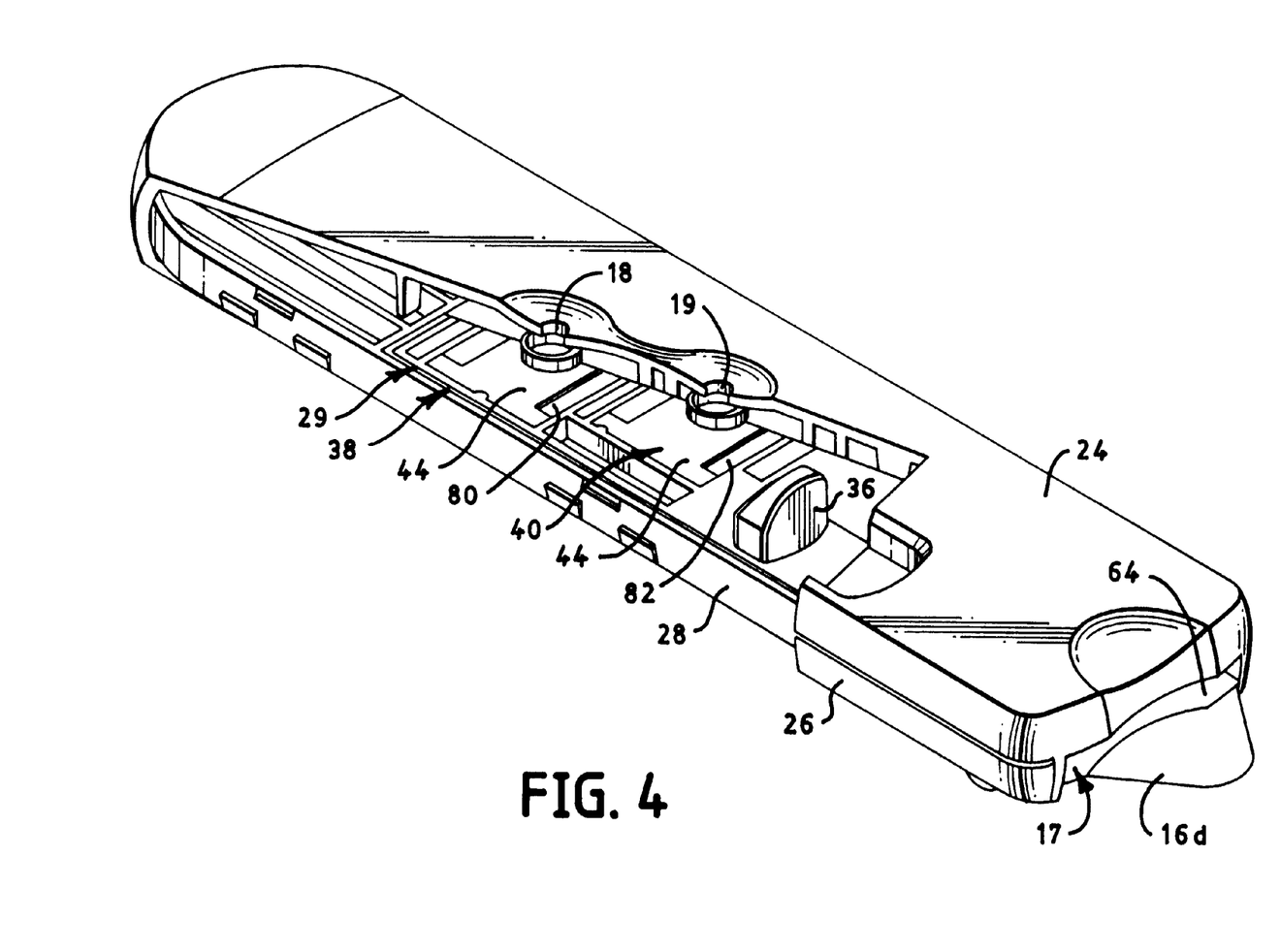
FIG. 4 is a perspective view similar to FIG. 1, but with components broken away to illustrate cooperation of interior components of the present invention.
Figure 5:
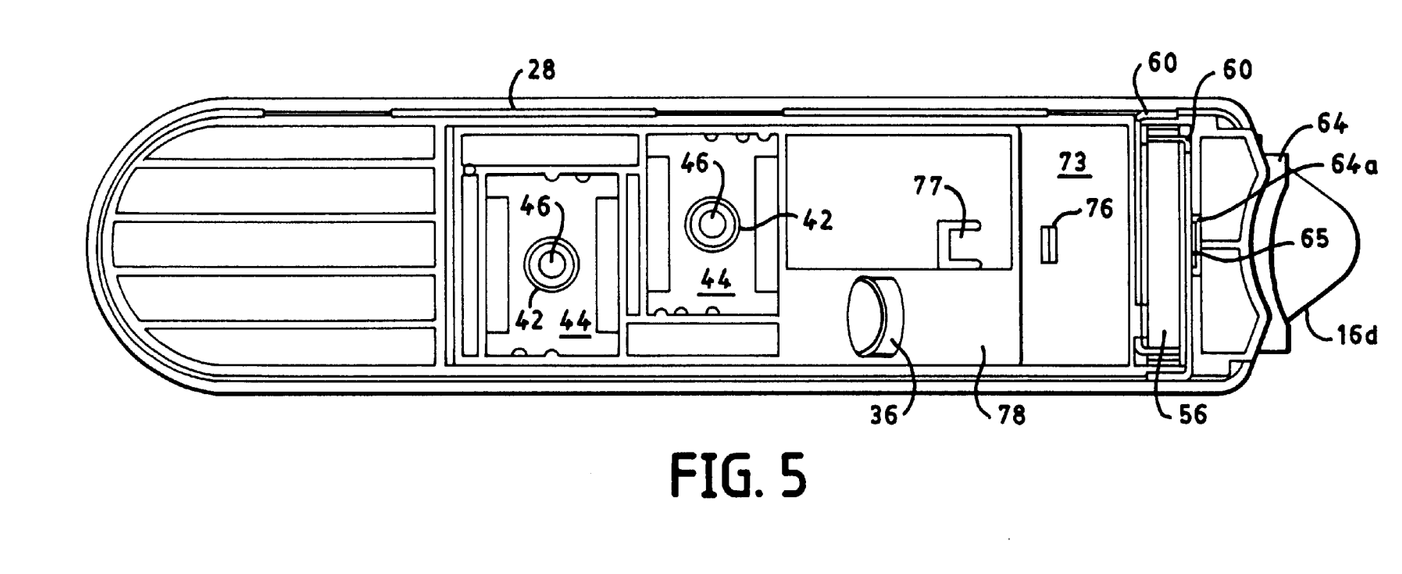
FIG. 5 is a top plan view illustrating details of several of the components of the present embodiment.

Reference is made back to the processor housing assembly 12 which includes a pair of generally rectangular upper and lower covers 24, 26 that sandwich therebetween a middle cover 28 and a carrier assembly 29 slidable therein. Ideally, the housing assembly is made from low-cost plastic materials, such as polystyrene and are opaque to facilitate light-blocking functions for image recording purposes. The upper cover 22 includes the pair of fluid access ports 18, 19 that are spaced apart from each other and are located in depressions of a contoured and depressed fluid receiving well 32. The fluid receiving well 32 is adapted to receive the body fluid (e.g., blood, saliva) to be tested and which is deposited or introduced thereinto during a testing procedure. The fluid travels to the assay elements as is best illustrated in FIG. 4. A slot 34 is formed to allow a tab 36 on the carrier assembly 29 to be advanced from a first accessing position to a second exposing position.

Figure 1:
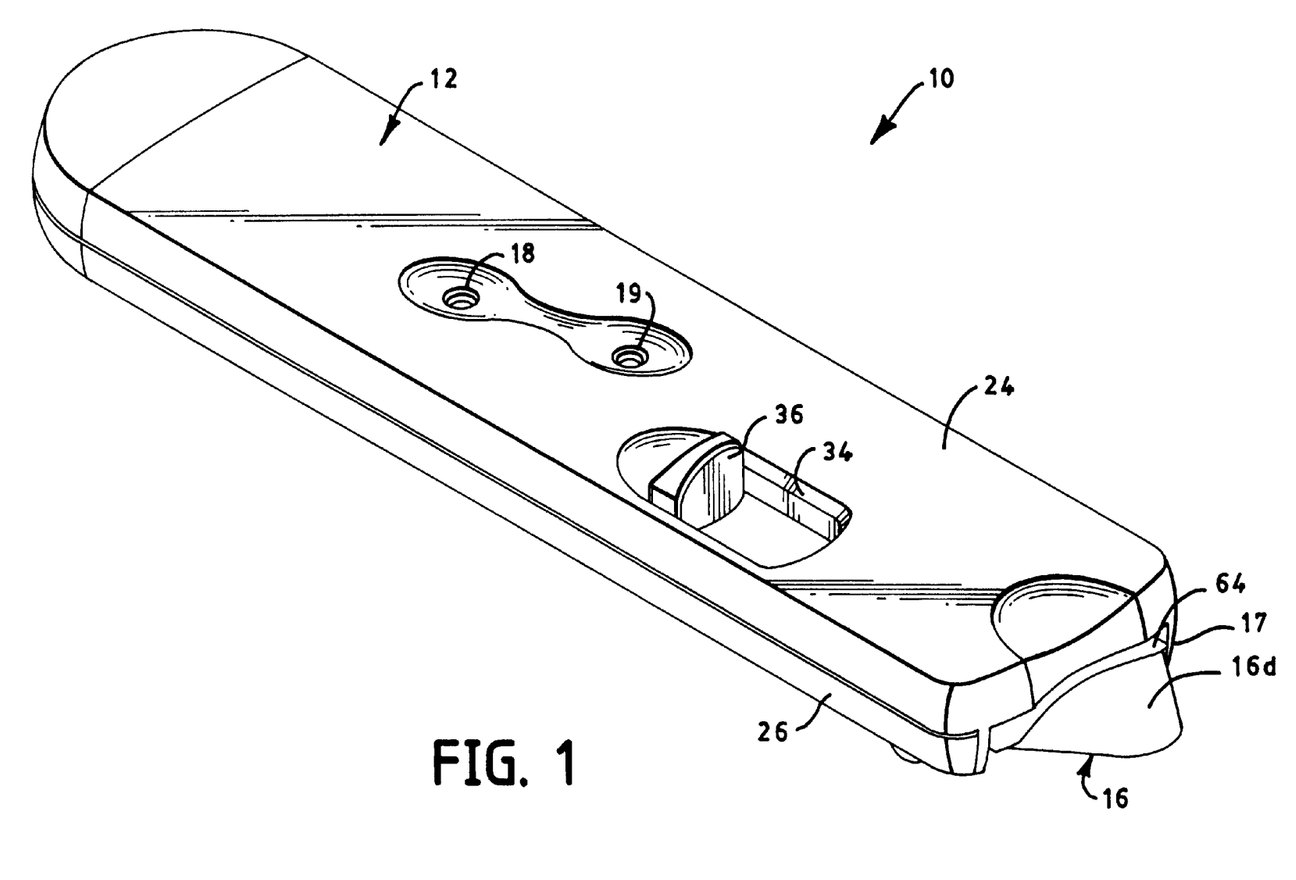
FIG. 1 is a perspective view of one of the embodiments of a diagnostic assay system of the present invention.
Figure 2:
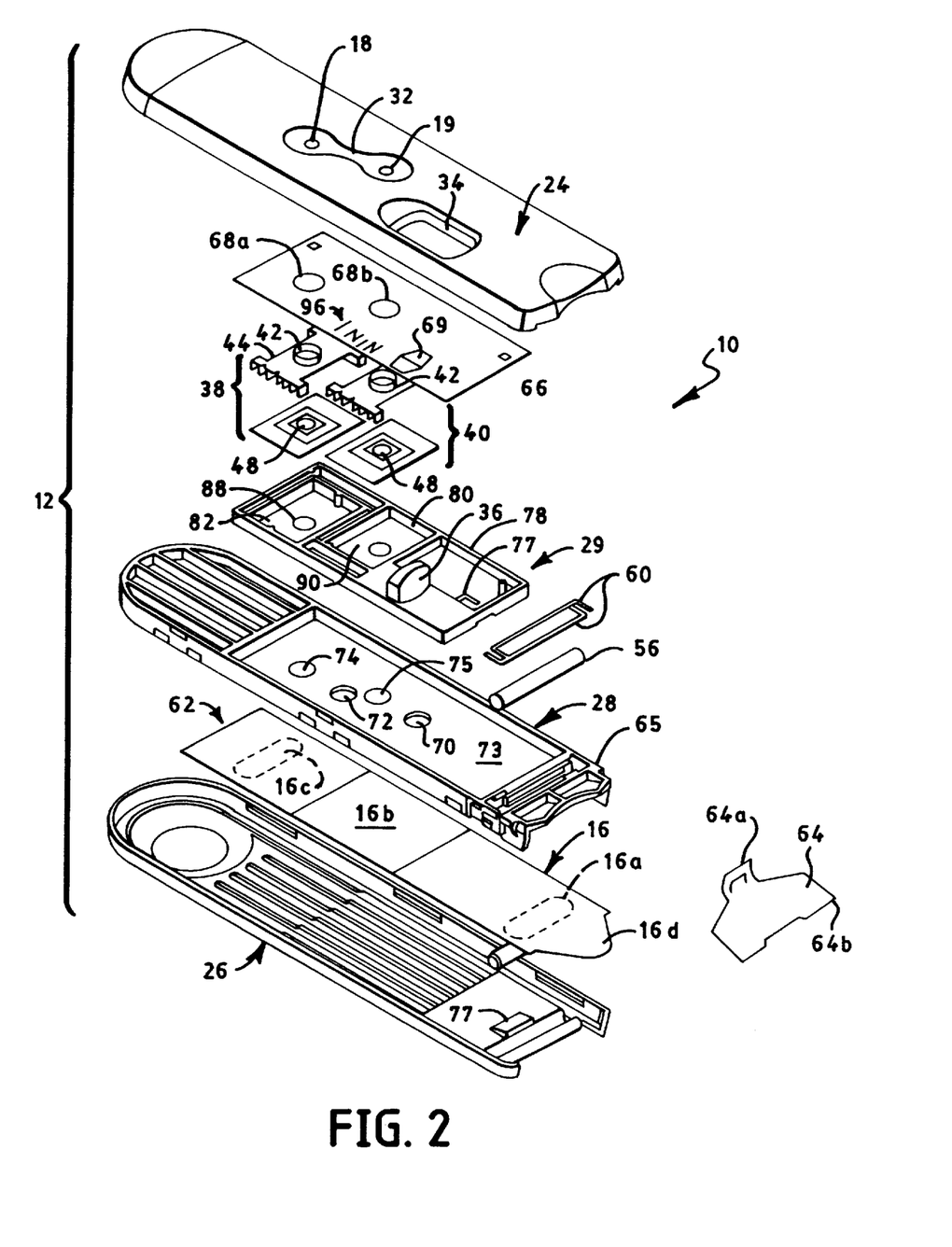
FIG. 2 is an exploded perspective view of the diagnostic assay system illustrated in FIG. 1.
Figure 3:
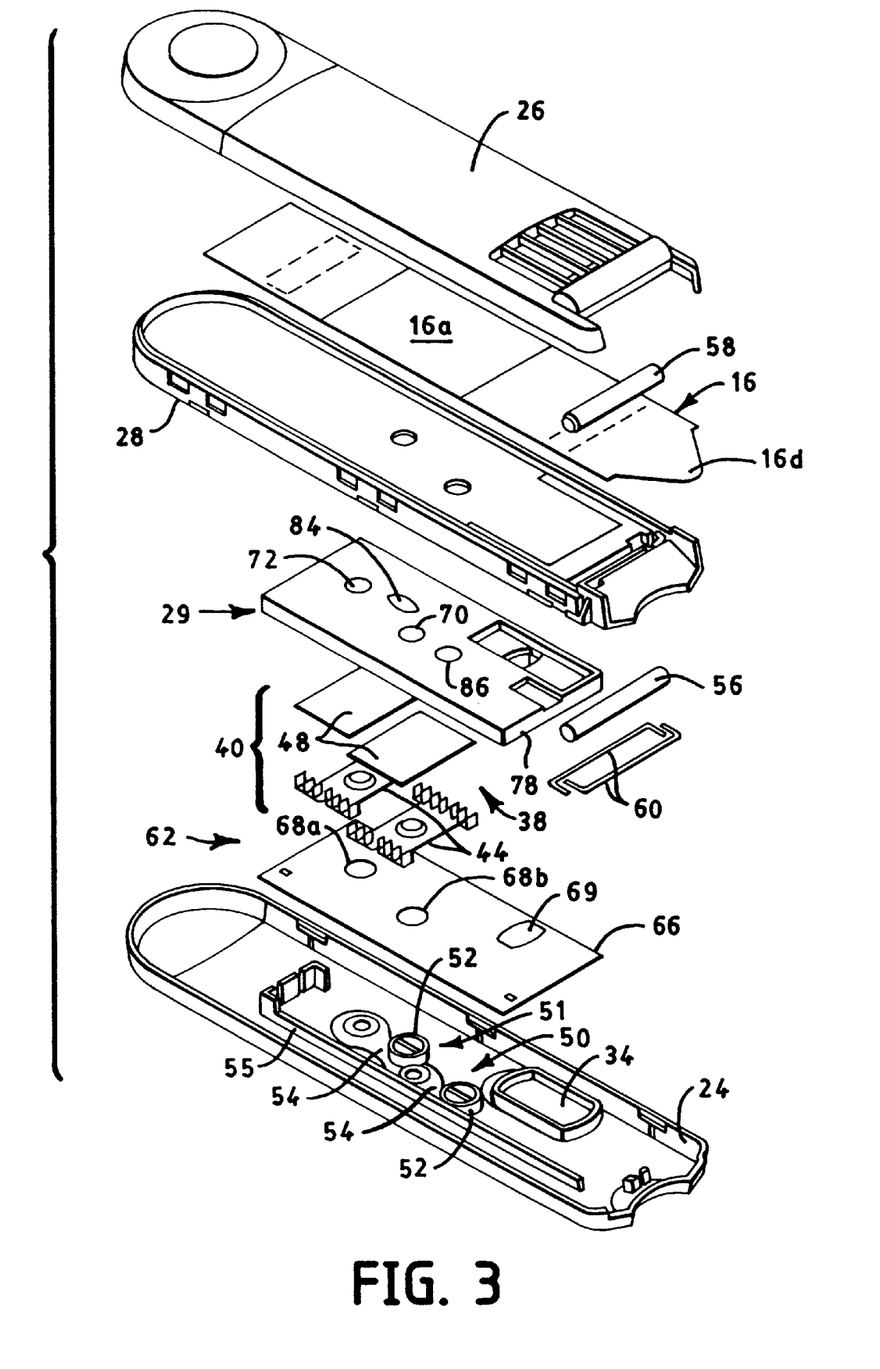
FIG. 3 is an exploded perspective view of similar to FIG. 2, but looking in the opposite direction.

As seen in FIG. 3, the biological diagnostic assay assembly includes test and control diagnostic assay devices 38,40; respectively. The diagnostic assay device 38 retains the deposited fluid and releases the test fluid upon demand, while the diagnostic assay device 40 retains and releases the test fluid upon demand for control purposes. The present embodiment also uses the term fluid reservoir assembly to describe the diagnostic assay device. The assay devices 38,40 do not, per se, form an aspect of the present invention of this embodiment, but are described in copending and commonly filed patent application (Atty. Dkt.8336) and the description thereof is incorporated herein as a part hereof. For purposes of understanding the present invention, however, only certain components are described herein. Each assay device includes a tubular well 42 for receiving the body fluid. The well 42 is centrally formed on a deflectable body member 44 with an assay porous material 46 attached to a bottom thereof. The porous material 46 functions to retain and release the body fluid in response to a triggering action to be described. Fluid release occurs when the assay porous material 46 is brought into engagement with an associated assay element 48, such as when a triggering force is applied to the deflecting member to deflect the porous material and diagnostic element into mutual engagement with each other. When such engagement occurs the retained fluid is released. The assay element 48 can be like that described in the last copending patent application (Atty. Dkt. 8336) and hence a detailed description thereof is not necessary. It is certainly within the spirit and scope of the present invention that a wide variety of fluid responsive diagnostic elements, preferably of the chemiluminescent type are contemplated for use.

On the interior surface of the upper cover 24 is a pair of triggering mechanisms 50, 51; each includes a tubular projection 52 with an inclined camming ramp 54 extending therefrom as illustrated to the inner surface of the cover. The tubular projections 52 are sized so as to encompass and nestle over the fluid wells 42 to provide a low-cost light labyrinth to prevent light from passing through the fluid and the apertures to the film when in the second position of the carrier assembly.

Reference is made to a film fluid processing assembly of the processor. It includes a spread roller 56 that is rotatably housed in the middle cover and which cooperates with a spread roller 58 that is rotatably housed in the lower cover to form a nip therebetween that releasably restrains the film frame within the housing; much as described in copending patent application Ser. No. 60/074,527. In this embodiment, the spread rollers may be defined by low-cost, steel dowel pins that are, preferably, rotatably mounted in cradles therefor. A pair of wire springs 60 are bent at opposite ends (U-shaped) and are mounted in mutually opposed and co-planar arrangement as depicted and cooperate with structure (FIG. 5) of the middle cover as well as the roller so as to serve to load the spread rollers together with adequate force to process an exiting film unit; as will be described. The middle portion of the springs are formed with a twist between the end legs to provide torsion. One end of the spring engages the one roller end and its opposite end is secured to the middle cover. Likewise one end of the other spring engages the opposite end of the roller. This spring arrangement provides a compact and inexpensive manner of loading the spread rollers. The spring biased rollers are biased to form a closed nip which simply and securely retains therein the film sheet such that the exposable portion 16b is positioned within a light-tight enclosure 62 defined by and between the middle and lower covers that are brought together in a snap-fit. As noted the tab 16d protrudes so as to extend from the processor housing assembly so that the film can be pulled. Hence, there is no need for separate film holding structure in the processor housing assembly. The present invention contemplates additional or substitute film-retaining structures. Accordingly, the film will not be dislodged until it is actively withdrawn from the processor housing assembly by the operator for processing purposes. To further assist in the light-blocking and light sealing of the film, provision is made for a flap 64 of thin flexible material, such as opaque Mylar™. One end has a hook 64a including a cut-out that is attached to a post 65 on the middle cover and the other end 64b is bent to extend through an opening (not shown) and from the exit 17 so as to engage the film to thereby minimize lightpiping as well as provide a light seal by deflecting the film below a bite line of the spread rollers.

To further assist in promoting light blocking functions provision is made for a rectangular and opaque sheet or blanket 66 that is adapted to travel with the carrier assembly 29 and serves to enhance light sealing of the process in the light-tight enclosure. Towards this end, a pair of spaced apart openings 68a, 68b is sized to fit snuggly over the respective the fluid wells 42, whereby the blanket is carried by the carrier assembly. A slot 69 is provided that allows the tab 36 of the carrier assembly 29 to extend therethrough. The underside of the upper cover includes a linear projection 55 that assists in holding the blanket in place.

Referring back to the lower cover 26, it has a snap fit to the middle cover and includes fluid spreading structure 77 similar to that shown in copending patent application 08/829,914. The lower cover 24 rotatably retains the lower spread roller 58. The upper and lower covers when mated act to prevent light from entering the enclosure 62 but act to define the film exit. The middle cover 28 includes a pair of field stops or apertures 70 and 72 formed on a planar surface 73 thereof which surface supports the carrier assembly for sliding movement. The apertures 70, 72 respectively communicate with the apertures 88, 90 when the latter are in the exposing position of the carrier assembly. A pair of raised circular detents 74, 75 are provided on the middle cover as well as a raised projection 76.

Reference is now made to the carrier assembly 29 which is defined as a generally rectangular slider body 78 having a pair of juxtaposed receiving wells 80, 82 having a configuration and size for respectively receiving the diagnostic assay devices 38,40 therein. A pair of circular depressions 84, 86 (FIG. 3) cooperate with the detents 74, 75 in the bottom of the carrier assembly 29 to releasably retain the latter in the first or fluid access position. The detenting action is overcome by virtue of the carrier assembly being slid to its second position. The latch 77 latches the projection 76 in order to prevent the slide from moving back to the original position. Aperture openings 88, 90 are formed in respective ones of the wells 80, 82 and are adapted to be in registry with the diagnostic assay devices in order to transmit the chemiluminescent response to the film within the light-tight enclosure 62.

After having explained the construction, the operation thereof is self-evident. However, to supplement the foregoing it will be appreciated that the system 10 of the present invention includes the processor housing assembly 12 that houses the preloaded pair of diagnostic assay devices 38, 40 in the receiving wells 80, 82 of slider 78. The slider 78 is normally held in the fluid access position by detenting provided by the detents 74, 75 so that the fluid wells 42 on the deflectable body members 44 are in registry with the ports 18, 19. The body fluid after being deposited will enter the ports 18, 19 and flow to the wells 42; as best seen in FIG. 4. The fluid is retained in the wells until it is desired to trigger the fluid release. Once it is desired to initiate the testing procedure, the tab 36 on the slider 78 is pushed by an operator to its second position. In the process, indicia 96 on the blanket 66 becomes visible to the operator through the slot 34. Such indicia can be used to instruct the user as to when to pull the film and commence processing of any latent images. During slider movement, the camming ramps 54 engage the fluid wells 42 of the test and control diagnostic test devices 38, 40 generally simultaneously and deflect the latter downwardly, whereby the porous material 46 engages the diagnostic element and cause a release of the fluid retained in the wells onto the diagnostic assay elements. It will be appreciated that the projections 52 nestle over the wells to further assist in light blocking functions. If an analyte of interest is present a chemiluminescent reaction signal is generated and the light emitted is directed to the film through the apertures 88, 90 which are in registry with the apertures 72, 70 of the middle cover. It will be appreciated that the apertures 70, 72 are uncovered during sliding movement of the slider 78. The control assay will also generate luminescent activity that will be imaged onto the film. After a predetermined time period elapses (e.g. 60 secs.) which period is selected in accordance with the anticipated luminescent activity to be generated, an operator can initiate development of any latent image(s) on the film. In this later regard, the operator can withdraw the film from the housing assembly. In the process, the spread rollers rupture the pod and the fluid is spread to initiate development of the film in a known manner. Accordingly, the operator can determine if image(s) are developed to indicate the presence or absence of the analyte of interest.

Figure 6:
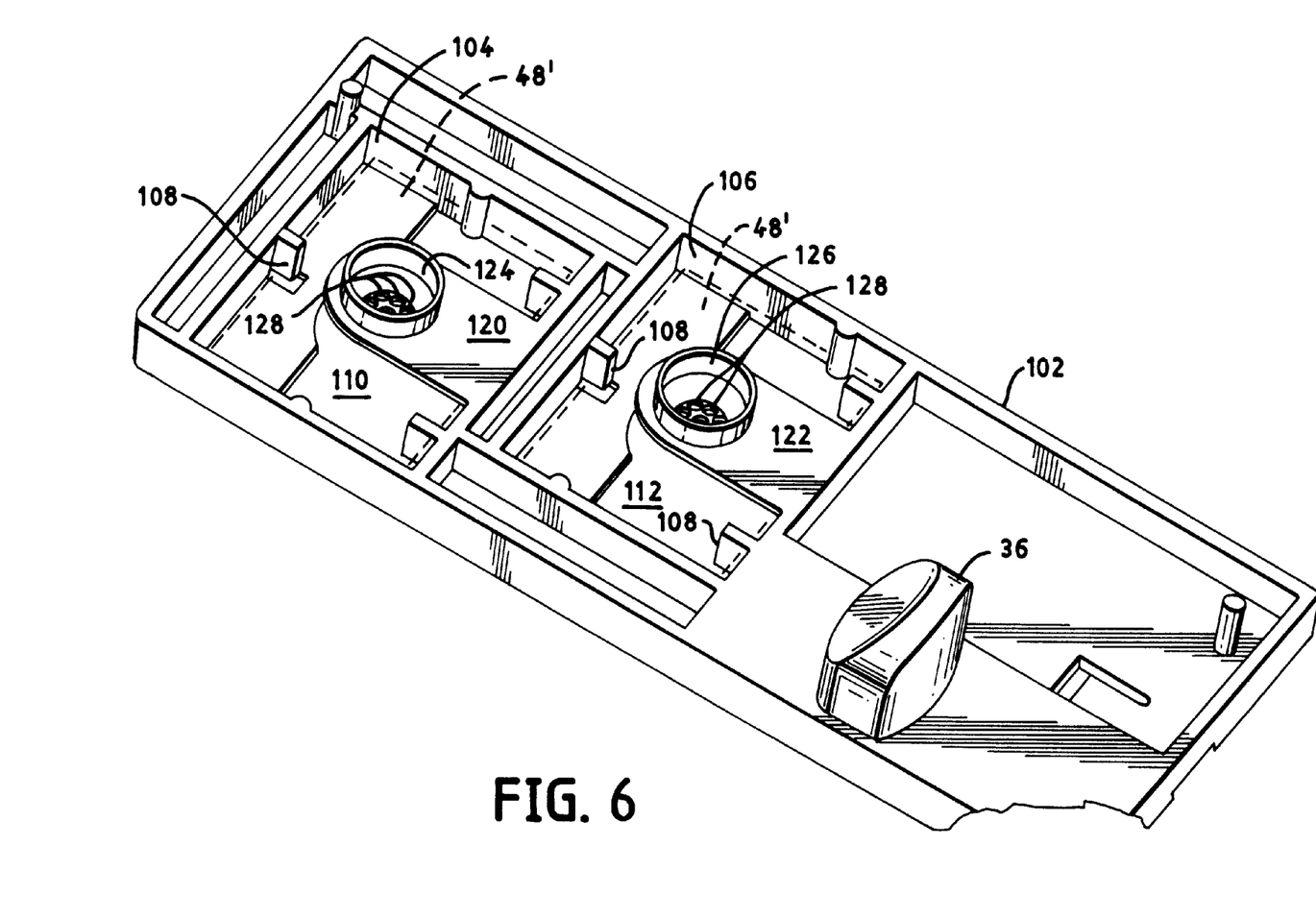
FIG. 6 is an enlarged perspective view of yet another embodiment of a carrier assembly of the present invention; and, FIG. 7 is a cross-sectional diagrammatic view of the carrier assembly in combination with a diagnostic system of the present invention.
Figure 7:
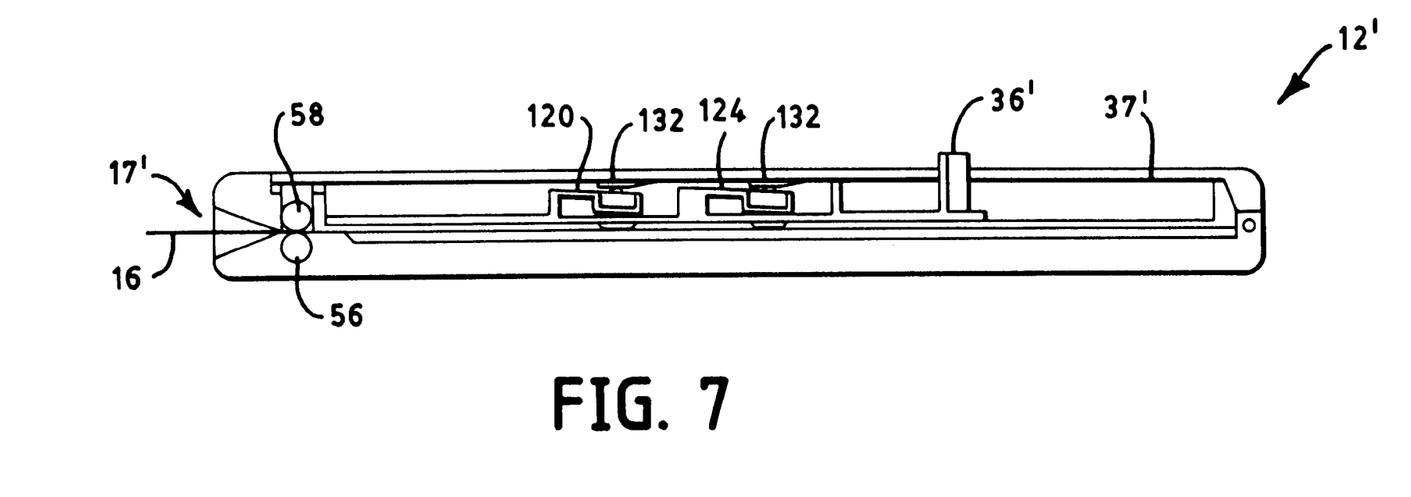

Reference is made to FIGS. 6 and 7 for illustrating another preferred embodiment of a diagnostic assay system 100 made according to the principles of the present invention. This version includes a fluid delivery system that stores and releases the fluid without the use of the porous material described above. As a consequence, an even more simple diagnostic system is provided that directly stores and releases the fluid upon demand. Structure of this embodiment that is similar to the other will be represented by like reference numerals with however the addition of a prime marking. Provision is made for a sample carrier assembly 102 having a generally elongated plastic base plate with a rectangular shape that is mounted for sliding movement in a processor housing 12' having a construction similar to that described above; but the difference therewith will be pointed out in the following description.

The sample carrier assembly 102 is housed for movement between the fluid accessing and exposing positions. Pushing on a slider tab 36' that protrudes through a housing slot 34' serves to move the carrier assembly between the two previously noted positions. The carrier assembly includes a pair of spaced apart test and control fluid assay receiving wells 104, 106; each for removably receiving and supporting a suitably dimensioned assay element 48'. The assay element 48' are retained under posts 108. The wells 104 and 106 include openings 110, 112 that will allow any signals generated on the assay elements to be transmitted to the openings 70', 72' in the middle cover.

A pair of cantilevered arms 120 and 122 is provided, each integrally connected to the sample carrier body 102 at their proximal ends and having fluid receiving cups 124 and 126; respectively, at their distal ends. The cups 124, 126 are centered over the diagnostic test elements and are adapted to separately receive therein both the test sample fluid whenever the sample carrier assembly is in its fluid receiving position. Each one of the receiving cups 124, 126 has a generally opened ended generally conical configuration having a capacity for storing an amount of fluid which is at least adequate for performing the testing intended. A plurality of spaced apart fluid orifices or openings 128 are formed adjacent the vertex of the cups. The openings 128 are appropriately sized and shaped in accordance with known parameters to define a meniscus through surface tension with the fluid and thereby establish means for storing the test sample fluid. The fluid is released when the meniscus in the openings engage the diagnostic element or in response to energy being otherwise applied to the fluid and/or the cup to overcome the surface tension or stated differently the molecular binding of the fluid and the cup. In this embodiment, the cup can be made of a preferably hydrophobic polymer, such as polypropylene or styrene. The fluid openings 128 are, preferably, sized and arranged to retain the fluid by reason of surface tension. In this embodiment, the openings are generally circular and have a diameter of about 0.040 in.; but this embodiment the diameter can vary in a range of from about 0.020 to about 0.060 inches. Although the openings 128 have the depicted configuration and described sizes, the present invention envisions different geometric shapes. Whatever shape is selected though, the dimensions thereof are selected in order to provide for retaining of the fluid by reason of surface tension; whereby a meniscus (not shown) is formed at each of the openings. The sizing and arrangement of the openings are such as to dispense evenly the fluid onto the assay test elements. As a consequence, fluid flows at a suitable rate through the openings and onto the assay element, thereby commencing a chemiluminescent reaction should the analyte of interest be contained in the sample fluid.

Reference is made to FIG. 7 for illustrating the housing assembly 12'. In this embodiment there is provided a pair of triggering cams 132 that depend from the interior of the upper cover. The cams 132 are adapted to engage an upper surface of the cups to thereby deflect the respective cantilevered arms as the sample carrier moves from the fluid receiving position to the exposing position. The arm deflection is sufficient to cause the fluid to contact the diagnostic element and overcome the surface tension. As a consequence, the fluid is dispensed onto the assay elements, thereby commencing a chemiluminescent reaction, should an analyte of interest be present in the sample fluid. Of course, the fluid also reacts with the control assay device element 48 to generate a control signal that can be recorded.

Although the invention has been described with respect to various preferred embodiments thereof, it is not intended to be limited thereto, but rather those skilled in the art will recognize that variations and modifications may be made therein which are within the spirit of the invention and scope of the appended claims.

What is claimed is:

1. A diagnostic assay system operable for conducting assay operations and recording signals generated therefrom; said system comprising: a hand-held processor housing assembly having at least one fluid access port and a light-tight compartment for a film assemblage; a film assemblage having its image recording area retained within a light-tight compartment and being withdrawable therefrom; a carrier assembly movable within the housing assembly between a fluid accessing position and an exposing position, the carrier assembly carries at a least fluid reservoir assembly for use in conjunction with an assay test element such that whenever in the fluid accessing position sample test fluid can be introduced through the access port; the fluid reservoir assembly retains fluid therein and releases the same upon demand onto the assay test element; a triggering assembly in the housing strikes the fluid reservoir assembly to release the fluid to the test strip when the carrier assembly moves to the exposing position thereby commencing a signal generating activity if the analyte of interest is present; and, means for allowing the signal to expose the film in the light-tight compartment when the carrier assembly is in the exposing position.

2. The system of claim 1 wherein the fluid reservoir assembly includes: a deformable member having an orifice extending therethrough; a porous material is joined to the deformable member for releasably holding a fluid sample within the orifice; the porous material is spaced from the assay element and when the deformable member is triggered the porous material engages the assay element and the fluid is released from the porous material.

3. The system of claim 1 wherein the fluid reservoir assembly includes a receptacle having at least one opening for forming a fluid meniscus so as to hold the fluid and then allow its release in response to a triggering action effected whereby the receptacle engages the assay element upon relative movement of the sample carrier assembly to housing assembly.

4. The system of claim 2 wherein the triggering assembly includes at least a camming member which engages the deformable member so as to deflect the latter and effect release of the fluid to the assay element as the carrier assembly moves from fluid accessing to the exposing positions.

5. The system of claim 4 wherein the means for allowing exposing of the film includes an exposure aperture, and the carrier assembly uncovers the exposure aperture as it is advanced to the exposing position.

6. The system of claim 1 wherein the film assemblage is of the self-developing type and comprises at least a single film unit is withdrawn from the housing assembly past film processing means located in the housing assembly so as to initiate development of latent images.

7. The system of claim 1 further including a second fluid reservoir assembly and corresponding triggering assembly for triggering the release of a control fluid introduced and retained in the second reservoir assembly to an associated assay strip in response to the sample carrier moving to the exposing position.

8. The system of claim 1 further including an opaque member which is carried by the carrier assembly to provide for light blocking.

9. The system of claim 1 wherein the triggering assembly covers the reservoir assembly for providing a light-blocking relationship when the carrier assembly is in the exposing position.

10. The system of claim 1 further including a diagnostic element that generates a signal in response to an analyte of interest contained in the fluid.

11. The system of claim 8 wherein the opaque member has indicia thereon that becomes visible through an opening in the housing assembly.

12. The system of claim 6 wherein the processing assembly includes biasing means for cooperating with a spread roller; said biasing means includes a pair of wire springs bent at opposite ends that are mounted in a mutually opposed and co-planar arrangement for resiliently urging opposing end portions of the spread roller with adequate force to process an exiting film unit.

13. A method of conducting a diagnostic assay of a test fluid and recording the results thereof by recording signals capable of exposing an image recording material if the test fluid contains an analyte of interest, said method includes the steps of: providing at least one self-developing film strip; providing a processor including a hand-held housing assembly having at least a fluid access port allowing introduction of the test fluid to a fluid reservoir assembly therefor and an associated diagnostic element in operative relationship thereto; housing the film assemblage within a light-tight compartment of the housing assembly so that an exposure aperture therein allows exposure of the film assemblage; carrying the fluid reservoir and diagnostic element in the housing from a first position to a second position; triggering the reservoir during such carrying step to release the retained fluid to the diagnostic element whereby if the fluid contains an analyte of interest a signal recordable on the film is generated; exposing the film assemblage through the exposure aperture when the diagnostic element is at the second position.

14. The method of claim 13 further including the step of processing the exposed film as the latter is withdrawn from the housing assembly.

15. The method of claim 13 wherein the step of carrying the fluid reservoir assembly and the diagnostic element is carried out by a sample carrier assembly which in the first position covers the exposure aperture and allows introduction of test fluid to the reservoir; and, in the second position uncovers the exposure aperture.

16. The method of claim 13 further including the step of: uncovering indicia in the housing assembly, which is visible through a slot in the housing assembly, when the carrier assembly moves from the fluid accessing position to the exposure position.

* * * * *